United States Patent [19]

Fenical et al.

[11] Patent Number: 5,444,043
[45] Date of Patent: Aug. 22, 1995

[54] CYCLIC HEPTAPEPTIDE ANTI-INFLAMMATORY AGENT

[75] Inventors: William H. Fenical, Del Mar; Robert S. Jacobs, Santa Barbara; Paul R. Jensen, San Diego, all of Calif.

[73] Assignee: The Regents of the University of California, Oakland, Calif.

[21] Appl. No.: 198,859

[22] Filed: Feb. 18, 1994

[51] Int. Cl.6 .................. A61K 38/12; A61K 38/00
[52] U.S. Cl. ............................. 514/9; 530/317; 530/321
[58] Field of Search ............... 530/317, 321; 514/9

[56] References Cited

U.S. PATENT DOCUMENTS

| Re. 32,455 | 7/1987 | Hamill et al. | 530/317 |
|---|---|---|---|
| 4,409,210 | 10/1983 | Kawaguchi et al. | 530/317 |
| 4,582,639 | 4/1986 | Matson | 530/317 |
| 4,885,243 | 12/1989 | Huber et al. | 435/71.3 |
| 4,977,083 | 12/1990 | Boeck | 530/317 |
| 5,028,590 | 7/1991 | Fukuda et al. | 514/11 |
| 5,138,036 | 8/1992 | Pettit et al. | 530/317 |
| 5,217,952 | 6/1993 | Kino et al. | 514/11 |
| 5,294,603 | 3/1994 | Rinehart | 514/11 |
| 5,336,757 | 8/1994 | Gulavita et al. | 530/317 |

*Primary Examiner*—Herbert J. Lilling
*Attorney, Agent, or Firm*—Poms, Smith, Lande & Rose

[57] ABSTRACT

A cyclic heptapeptide anti-inflammatory agent named cyclomarin-A is disclosed.

Cyclomarin-A is produced by a specific marine actinomycete. The cyclomarin-A producing bacterium is isolated from sediment located in marine estuaries in and around San Diego, Calif. Fermentation of the isolated bacterium in saltwater-based media produces cyclomarin-A as a secondary by-product. The cyclomarin-A is useful as an anti-inflammatory agent.

5 Claims, 3 Drawing Sheets

CYCLIC HEPTAPEPTIDE ANTI-INFLAMMATORY AGENT

BACKGROUND OF THE INVENTION

This invention was made with Government support under Grant No. CA-44848, awarded by the National Institutes of Health. The Government has certain rights in this invention.

1. Field of the Invention

The present invention relates generally to marine bacteria which produce anti-biotics, anti-inflammatory agents and associated pharmacologically-active compounds. More particularly, the present invention relates to the discovery and isolation of a particular marine bacterium which, when subjected to fermentation in seawater-based media, is capable of producing a cyclic heptapeptide that is an effective anti-biotic and anti-inflammatory agent.

2. Description of Related Art

There is a growing interest in investigating diverse classes of marine bacteria to determine their ability to produce secondary metabolites that are useful as drugs or pharmaceutical agents. Terrestrial actinomycetes are one type of bacteria which are known to produce a large number of antibiotic and associated compounds. Related bacteria are known to exist in various marine habitats including the surfaces of marine animals and plants (Fenical, W. *Chem. Rev.* 1993, 93, 1673-1683; Gil-Turnes, M. S., Hay, M. E., Fenical, W. *Science* 1989, 246, 116-118; and Gil-Turnes, M. S., Fenical, W. *Biol. Bull.* 1992, 182,105-108). The actinomycetes are also found in shallow water marine sediments (see Jensen, P. R., Dwight, R., Fenical, W. *Appl. Environ. Microbiol.* 1991, 37, 1107-1108).

Some of the secondary metabolites produced by marine actinomycetes have been found to possess antibiotic properties. For example, see Pathirana, C., Jensen, P. R., Fenical, W. *Tetrahedron Lett.* 1993, 33, 7663-7666; Pathirana, C., Jensen, P. R., Dwight, R., Fenical, W. *J. Org. Chem.* 1992, 57, 740-742; and Okami, Y., Hopita, K., Yoshida, M., Ikoda, D., Kondo, S., Umozawa, H. J. *Antibiot.* 1979, 32, 964-966. Other secondary metabolites have been found to possess anti-tumor properties (see Tapiolas, D. M., Roman, M., Fenical, W., Stout, T. J., Clardy, J. J. *Am. Chem. Soc.* 1991, 115, 4682-4683; and Takahashi, A., Kurosawa, S., Ikeda, D., Okami, Y., Takeuchi, T. J. *Antibiot.* 1989, 42, 1556-1561).

Although some marine bacteria have been isolated which are capable of producing antibiotics and antitumor agents, there is a continuing need to discover and isolate additional marine bacteria that are capable of producing secondary metabolites which are useful as pharmaceutical agents. In addition, there is a continuing need to provide new methods for fermenting marine bacteria to optimize production of useful secondary metabolites.

SUMMARY OF THE INVENTION

In accordance with the present invention, a new marine bacterium has been discovered and isolated from sediments found in marine estuaries located in southern California. The bacterium is a *Streptomyces sp.* actinomycete. It was discovered that fermentation of the bacterium in seawater-based media resulted in the production of a secondary metabolite which is useful as an anti-inflammatory agent. The metabolite is a cyclic heptapeptide which has been given the name cyclomarin-A.

Cyclomarin-A has the structure

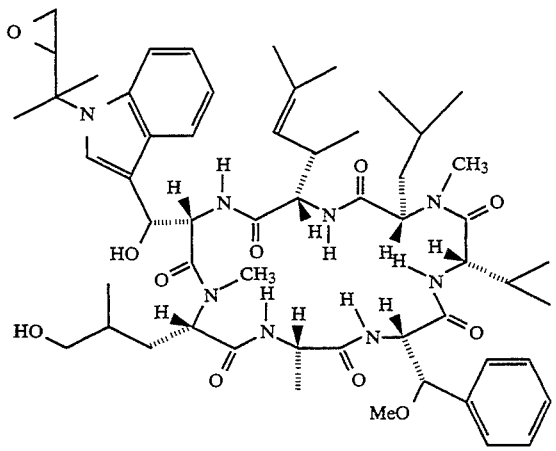

As a feature of the present invention, cyclomarin-A may be used alone or in combination with a variety of pharmaceutical carriers to form compositions which are useful for treating inflammation of tissue.

The above discussed and many other features and attendant advantages of the present invention will become apparent as the invention becomes better understood by reference to the following detailed description when taken in conjunction with the accompanying drawings.

DESCRIPTION OF THE PREFERRED EMBODIMENTS

The new compound discovered in accordance with the present invention is a cyclic heptapeptide.

The structure of cyclomarin-A is

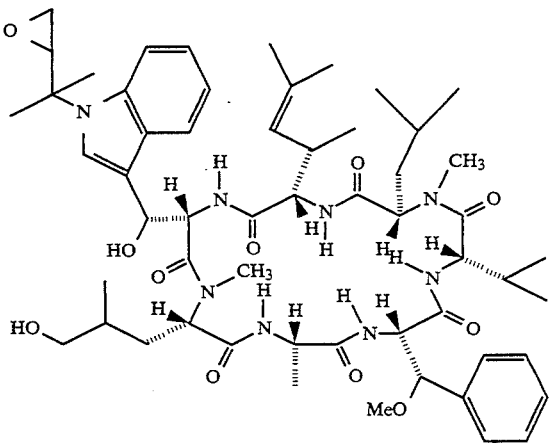

Cyclomarin-A is a metabolite of *Streptomyces sp.* which is obtained by EtOAc extraction of the saline fermentation broth. The molecular formula for cyclomarin-A is $C_{56}H_{82}O_{11}N_8$ as determined by $^1H$, $^{13}C$ NMR and high resolution FAB mass data.

Figure 2:
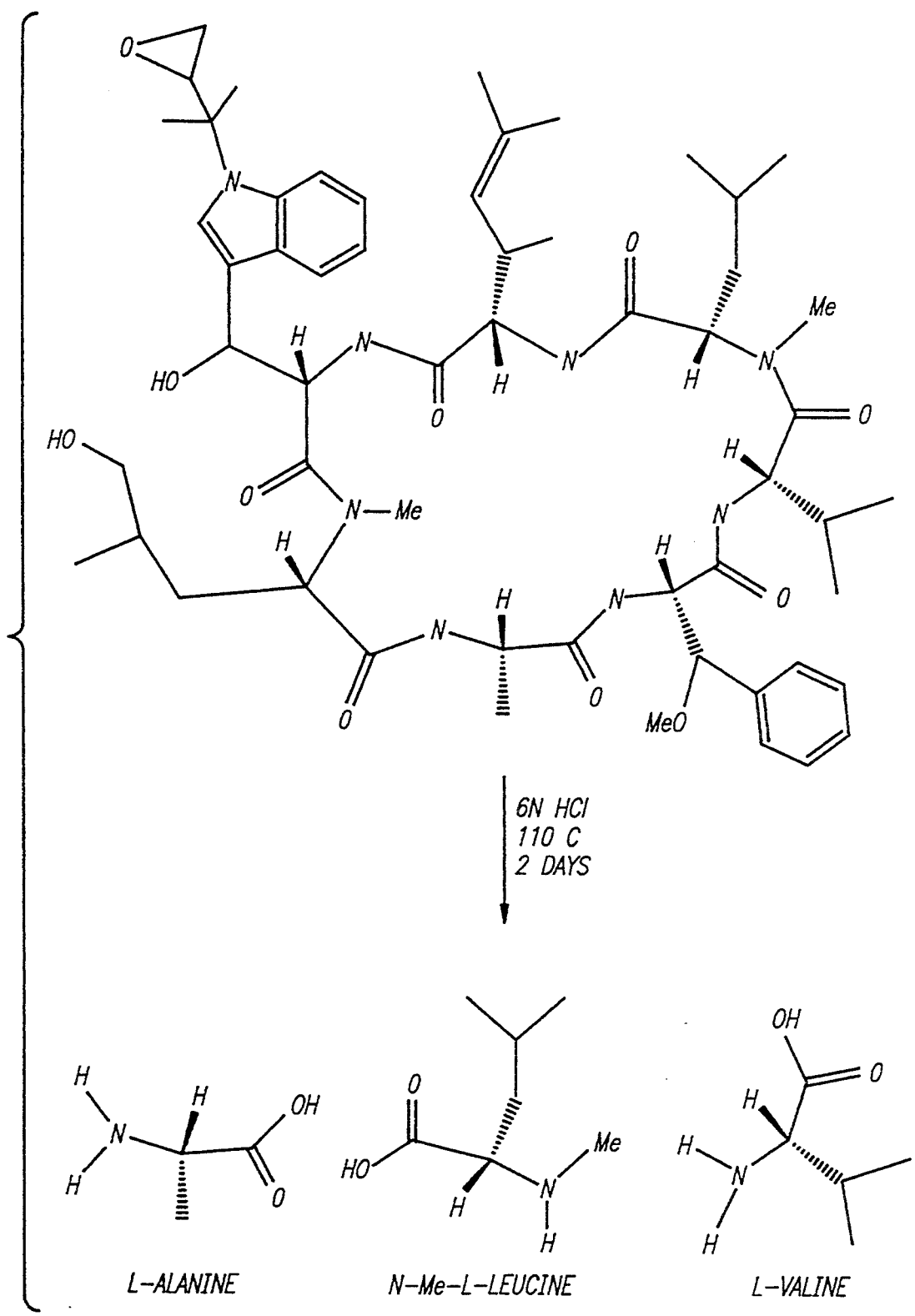
FIG. 2 depicts the results of acid hydrolysis of cyclomarin-A.

Cyclomarin-A is a white or colorless fine crystal, $[\alpha]_D$-52(CHCl$_3$). UV absorption bands at 293, 287 and 222 indicate indolic and benzylic chromophores. This is supported by the infra-red spectrum, which shows strong bands of amino carbonyl at 1644 cm$^{-1}$, and aromatic absorptions at 1512 and 1453 cm$^{-1}$. In addition, the occurrence of NH and OH functionalities is indicated by a strong band between 3300 and 3400 cm$^{-1}$. The $^1H$ NMR spectral data of cyclo-marin-A in DMSO-d$_6$ exhibited 82 proton signals, in which seven protons (δ 9.20, 8.99, 8.38, 8.29, 7.15, 5.82, 4.04), were assigned as either NH or OH due to lack of carbon correlation in a heteronuclear correlation NMR (HMQC) analysis. The $^{13}C$ NMR spectrum, showing 7 carbonyl signals (δ 172.54, 171.59, 171.0, 170.6, 169.61, 1168.85, 168.42) and characteristic signals for peptide demonstrate that cyclomarin-A is a heptapeptide. Several ninhydrin positive spots on thin layer chromatography (TLC) upon acid hydrolysis are generated. The stereochemistry of the standard amino acid residues were determined by chiral TLC coupled with detection of $^1H$ NMR allowing us to assign the L configuration for the alanine, valine, and N-methyl-leucine residues (see FIG. 2).

Figure 1:
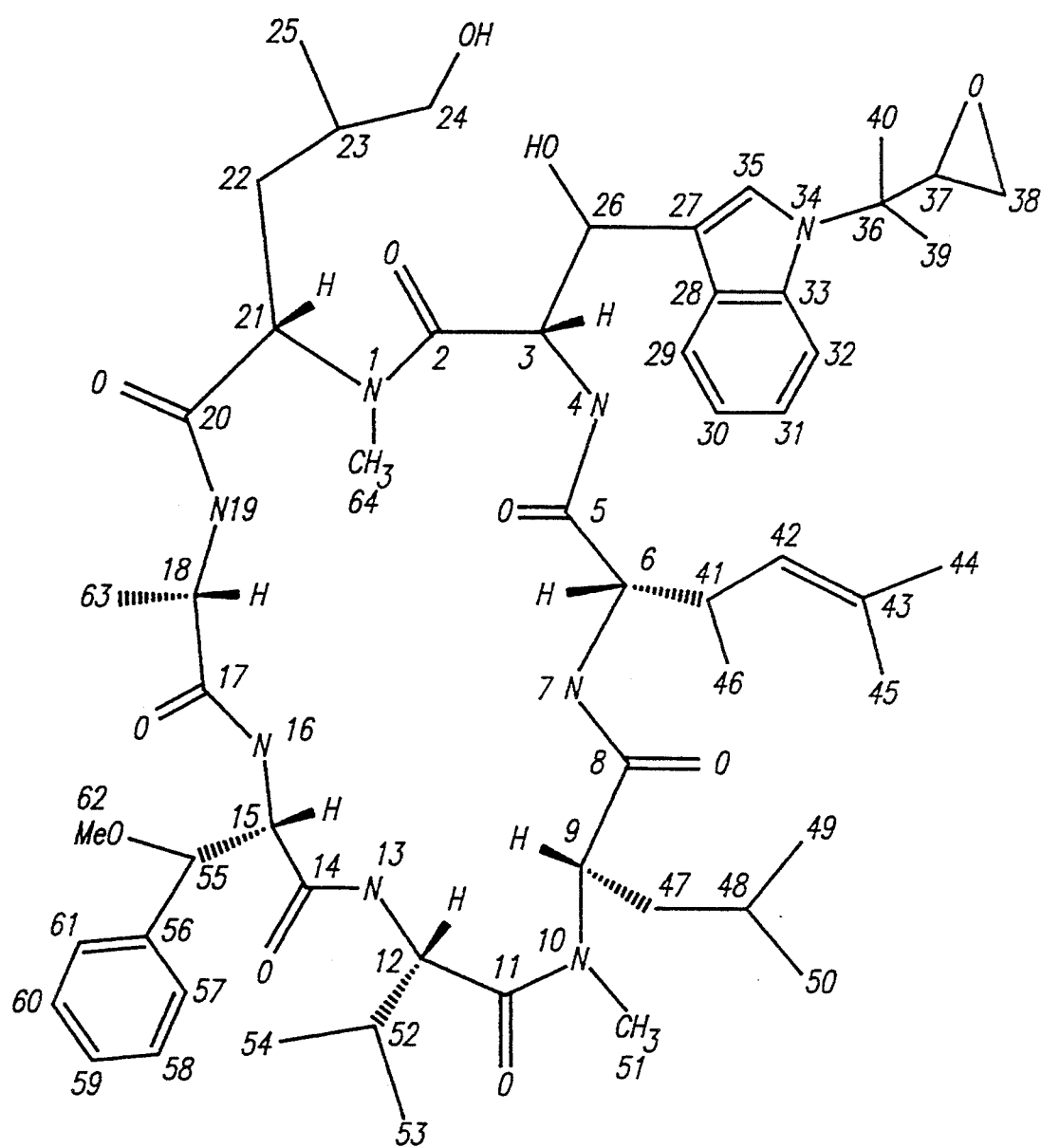
FIG. 1 depicts the structure and numbering sequence for cyclomarin-A.

The $^1H$ $^{13}C$ NMR and homonuclear correlation NMR (COSY), heteronuclear correlation NMR (HMBC) correlation data of cyclomarin-A are listed in Table 1. The carbon members in Table 1 correspond to the numbered carbons in the formula for cyclomarin-A set forth in FIG. 1.

TABLE 1

$^{13}C$ AND $^1H$ NMR DATA FOR CYCLOMARIN-A

| C# | δ$^{13}$C | 1-H | δ$^1$H |
|---|---|---|---|
|  |  | 4 (NH) | 6.90 d (3.5) |
|  |  | 7 (NH) | 8.10 d (9) |
|  |  | 13 (NH) | 7.99 d (8) |
|  |  | 16 (NH) | 7.14 d (5) |
|  |  | 19 (NH) | 8.19 d (10) |
| 2 | 171.0 s |  |  |
| 3 | 52.79 d | 3 | 4.60 dd (4, 3.5) |
| 5 | 172.54 s |  |  |
| 6 | 58.08 d | 6 | 4.12 t (1 0) |
| 8 | 168.42 s |  |  |
| 9 | 58.63 d | 9 | 4.83 t (7) |
| 11 | 170.59 s |  |  |
| 12 | 55.25 d | 12 | 4.38 dd (9, 8) |
| 14 | 169.61 s |  |  |
| 15 | 55.89 d | 15 | 4.91 t (5) |
| 17 | 171.59 s |  |  |
| 18 | 50.63 d | 18 | 4.85 m |
| 20 | 168.84 s |  |  |
| 21 | 59.31 d | 21 | 4.78 m |
| 22 | 33.07 t | 22 | 0.60 m, 2.26 m |
| 23 | 33.21 d | 23 | 1.42 m |
| 24 | 66.42 t | 24 | 3.15 dd (11.5, 6) |
|  |  |  | 3.22 dd (11.5, 4) |
| 26 | 68.53 d | 26 | 5.31 d (4) |
| 27 | 111.92 s | 27 |  |
| 28 | 126.91 s |  |  |
| 29 | 119.08 d | 29 | 7.60 d (8) |
| 30 | 119.82 d | 30 | 7.09 t (8) |
| 31 | 122.12 d | 31 | 7.18 t (8) |
| 32 | 113.66 d | 32 | 7.72 d (8) |
| 33 | 136.05 s |  |  |
| 35 | 123.35 d | 35 | 7.32 s |
| 36 | 58.13 s | 36 |  |
| 37 | 57.75 d | 37 | 3.21 dd (4.5, 3) |
| 38 | 45.44 t | 38 | 2.89 t (4.5) |
| 39 | 23.08 q | 39 | 1.56 s |

TABLE 1-continued $^{13}C$ AND $^1H$ NMR DATA FOR CYCLOMARIN-A

| C# | δ$^{13}$C | 1-H | δ$^1$H |
|---|---|---|---|
| 40 | 24.45 q | 40 | 1.65 s |
| 41 | 35.54 d | 41 | 1.70 m |
| 42 | 124.78 d | 42 | 4.76 d (10) |
| 43 | 134.47 s |  |  |
| 44 | 25.73 q | 44 | 1.71 s |
| 45 | 18.88 q | 45 | 1.27 s |
| 46 | 18.51 q | 46 | 0.65 d (6.5) |
| 47 | 38.90 t | 47 | 2.26 m |
| 48 | 25.05 d | 48 | 1.40 m |
| 49 | 22.38 q | 49 | 0.84 d (7) |
| 50 | 23.49 q | 50 | 0.88 d (6.5) |
| 51 | 29.54 q | 51 | 2.83 s |
| 52 | 30.84 d | 52 | 2.25 m |
| 53 | 19.29 q | 53 | 1.06 d (7) |
| 54 | 20.0 q | 54 | 0.94 d (7) |
| 55 | 79.94 d | 55 | 5.06 d (5.5) |
| 56 | 135.14 s |  |  |
| 57, 61 | 127.84 d (2C) | 57, 61 | 7.18 (2H) |
| 58, 60 | 128.34 d (2C) | 58, 60 | 7.22 (2H) |
| 59 | 128.70 d | 59 | 7.25 |
| 62 | 57.78 q | 62 | 3.36 s |
| 63 | 20.83 q | 63 | 1.28 d (6.5) |
| 25 | 17.74 q | 25 | 0.70 d (7) |
| 64 | 29.29 q | 64 | 2.71 s |

Figure 3:
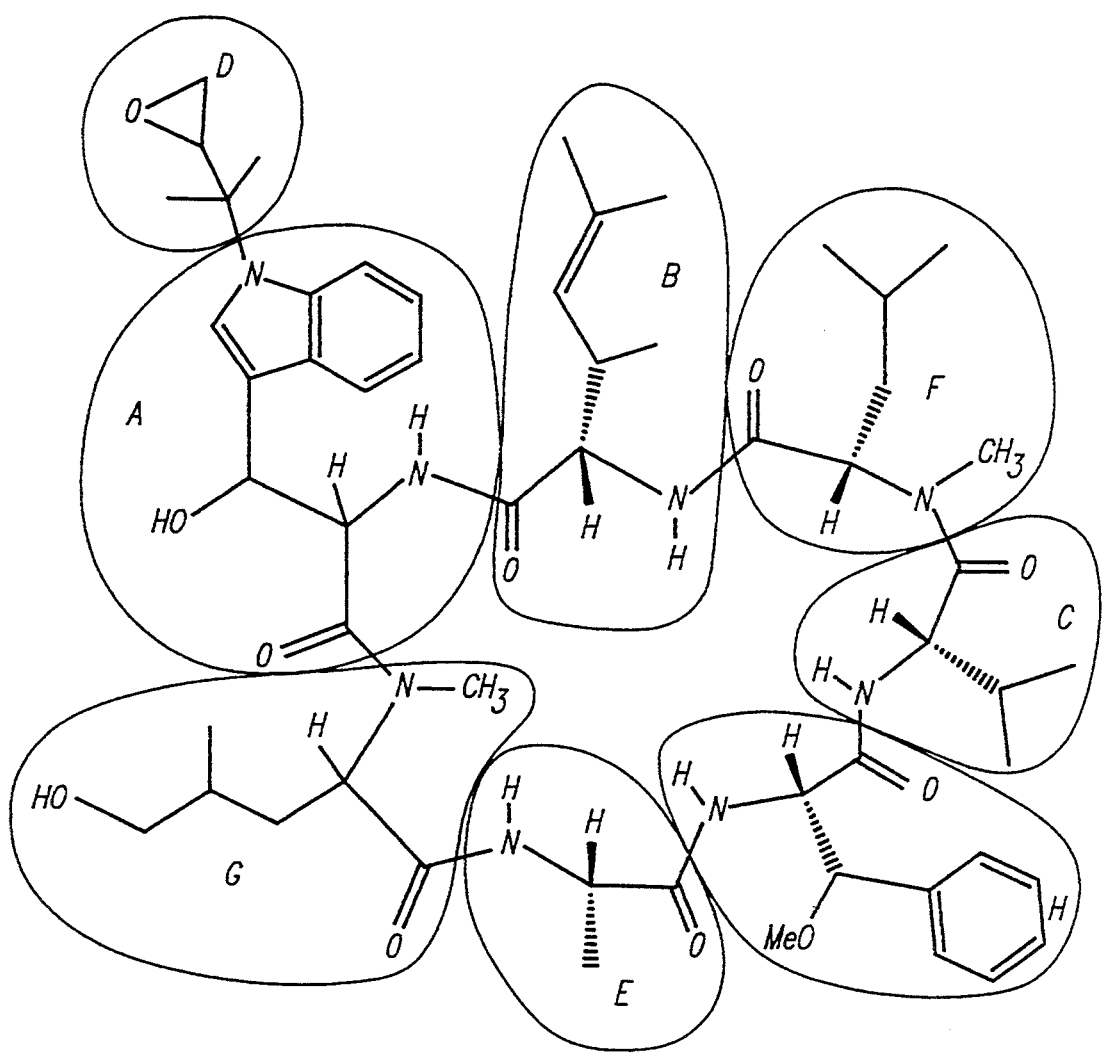
FIG. 3 depicts the formula and mass spectral fragmentation of cyclomarin.

The results from extensive nuclear Overhauser enhancement (NOE) and 2D NMR experiments established the seven partial structures shown in FIG. 3. Units A, B, G and H are uncommon amino acids while the other 3 amino acid units (C, E and F) are common ones. Unit D is an isoprenyl group. Among them, correlations present in the COSY 45 and HMBC spectrum optimized at 6 Hz, showed cross peak connectivities for the C, H-α and amide proton as well as the side-chain spin system of alanine (E): H-18 (δ 4.85), H-19 (δ 8.19), H-63 (δ 1.28), C-18 (δ 50.63), C-17 (δ 171.6), C-63 (δ 20.83); valine (F): H-12 (δ 4.38), H-13 (δ 7.99), H-52 (δ 2.25), H-53 (δ 1.06), H-54 (δ 0.94); N-methyl-leucine (C): H-9 (δ 4.83), H-47 (δ 2.26), H-48 (δ 1.40), H-49 (δ 0.84), H-50 (δ 0.88), H-51 (δ 2.83), C-8 (δ 168.42), C-9 (δ 58.63), C-47 (δ 38.9), C-48 (δ 25.05), C-49 (δ 22.38), C-50 (δ 23.49), C-51 (δ 29.54). The remaining units, however, are β-hydroxytryptophanyl (A), β-methyl β-isobutyl 1-ene-alanyl (B), N-methyl δ-hydroxyleucyl (G), O-methyl-phenylseryl (H), and isoprenyl (D) units.

The signals for the unit A were assigned by interpreting the COSY, HMBC and NOE spectra. First of all, a AMX spin system was composed by 4-NH (δ 6.90) 3-H (δ 4.60) and an oxygenated C-26 proton (δ 5.31). This was supported by the observation of HMBC correlation between C-2 carbonyl (δ 171.0) and 3-H, 26-H. Second, two separated doublets (29-H, δ 7.72; 32-H, δ 7.60) on the indole moiety were coupled respectively with two triplets at δ 7.09, 7.18 (30-H, 31-H). By HMBC, 26-H was found to correlate with C-35 (δ 123.35), C-37 (δ 57.75), and C-28 (δ 126.91) simultaneously. In addition, by NOE, the signal at 29-H (δ 7.60) was enhanced when 26-H (δ 5.31) and 3-H (δ 4.60) were irradiated. The unit B is also an uncommon amino acid too. The amide proton at δ 8.10 (7-NH) was correlated with 6-H (δ 4.12), which in turn showed correlations with C-5 (δ 172.54) and C-41 (δ 35.54) by HMBC, and correlations with 46-methyl doublet (δ 0.65) and the olefinic 42-H (δ 4.76) by NOE. Correlation between 41-H (δ 1.70) and 42-H (δ 4.76) by NOE. Correlation between 41-H (δ 1.70) and 42-H, and 46-Methyl doublet were also found. Meanwhile, irradiation of both the 44-Methyl singlet (δ

1.71) and 46-methyl doublet (δ 0.65) caused enhancements of 42-H (δ 4.76), which showed correlation with C-44 (δ 25.73) and C-45 (δ 18.88). The isoprene unit (δ) contains an ABX spin system (d 3.20, 2.85, 2.75), in which both C-37 (δ 57.75) and C-38 (δ 45.44) are oxygenated. The 37-H (δ 3.21) was correlated with the quaternary C-36 (δ 58.13), which was simultaneously correlated with two germinal methyl singlets at δ 1.56, 1.65 (C-39, C-40) by HMBC methods. As for unit G, no amide proton was found. Instead, an N-methyl singlet at δ 2.71 (64-H) showed correlation with C-21 at δ 59.31. Moreover, the 21-B (δ 4.78) correlated with the carbonyl C-20 (δ 168.84), C-22 (δ 33.07), and C-64 (δ 29.29). COSY data established connectivities between H-21, H-22(δ0 0.60, 2.26), H-23(δ 1.42), H-24 (δ 3.15, 3.22) and H-25 (δ 0.70). Also, this finding was confirmed by HMBC and NOE studies. The established unit G is N-methyl-δ-hydroxyleucine, which can be prepared via 1,4-Michael addition of azlactone (E-P. Sabine, *Tetrahedron*, 45(19), 6127 (1989)). Using the same approach, the last one (unit H) was established as O-methylphenylserine, which is a known synthetic product (S. Iriuchijima, K. Maniwa and G-I Tsuckihashi, *J. Am. Chem. Soc.*, 96 (13), 4280 (1974)). The 15-H (δ 4.91) showed correlation with both 16-NH (δ 7.14) and 55-H (δ 5.06) by COSY, and correlations with carbonyl C-14 (δ 169.61) and C-56 (δ 135.14) by HMBC. Both the methoxy and phenyl moieties located at position C-55 were confirmed by $^{13}C$ HMBC and NOE data.

The absence of an ester band in the IR spectrum confirms that all seven carbonyls are amide bonds. The sequence of these amino acids and the location of the isoprene unit were established primarily by HMBC and NOE methods and further confirmed by E1 mass fragmentation studies of cyclomarin-A. The HMBC correlation between carbonyl C-2 (δ 171.0) and 64-N-methyl singlet (δ 2.71) together with the enhancement of 3-H (δ 4.60) by irradiation of 21-H at 4.78 indicated the amide bond between N-1 and C-2. Correlation between the carbonyl C-5 (δ 172.54) and 4-NH (δ 6.90) as well as NOE between 4-H and 6-H (δ 4.12) confirms that an amide bond is located between N-4 and C-5. Further, observation of an HMBC correlation between 6-H and N-7-H (δ 8.10) with C-8 (δ 168.42) and an NOE between N-7-H and 9-H (δ 4.83), as well as an NOE between 46-methyl protons (δ 0.65) and methyl singlet (δ 2.83) of N-methyl leucine indicated connectivity between N-7 and C-8. The NOE enhancement between 9-H and 12-H (δ 4.38), as well as HMBC correlation between C-11 (δ 170.6) and N-10-methyl (δ 2.83) reflected an amide link between N-methyl leucine and valine. Both α-H (δ 4.38) and N-13-H (δ 7.99) of valine were correlated with C-14 (δ 169.61) of O-methyl phenyl serine indicating they were connected. This was confirmed by NOE observations between N-13-H and the phenyl protons (57, 61-H, δ 7.18). The HMBC correlation among C-17(6 171.59), N-16-H(6 7.14) and 15-H (δ 4.91) as well as signal enhancement of 58-H (δ 7.22) and 61-H (δ 7.22) by irradiation of C-36 methyl doublet (δ 1.28) on alanine suggested connectivity between O-methyl phenyl serine and alanine. Furthermore, an amide bond between alanine and δ-hydroxy-N-methyl leucine was determined by the correlation between N-19-H (δ 8.19) and C-20 (δ 168.84). This sequence analysis established that cyclomarin-A is a cyclic-heptapeptide.

The remaining isoprene unit located at N-34 position of indole moiety was confirmed by NOE experiments. Irradiation of both the methyl singlets (39-H and 40-H) caused enhancements of 32-H (δ 7.72) and 35-H (δ 7.32), and vise-versa. The chemical shifts of the C-37 methine proton (δ 3.20) and the C-38 methylene protons (δ 2.85, 2.75), as well as the coupling constants (4.5 Hz, 3 Hz, 4.5 Hz) between these protons suggested an epoxide ring. This finding was supported by an IR absorption at 3030 $cm^{-1}$ and by the EI mass spectrum of cyclomarin-A, which showed a fragment ion at m/z 85.

Acetylation of cyclomarin-A provided a diacetate which exhibited two acetyl singlets at δ1.90 and 2.10. The 26-H doublet of the diacetate derivative was shifted 1 ppm from δ 5.31 to δ 6.45. The $^{13}C$ spectrum of the diacetate derivative showed downfield shifts of C-26 (δ 72.03) and C-24 (δ 68.96), and upfield shift of C-23 (δ 28.38), C-25 (δ 15.23) and C-27 (δ 107.79) when comparing with those of cyclomarin-A.

The electron-impact mass (EIMS) spectrum of cyclomarin-A showed characteristic ions at m/z 814 (loss of an isoprene unit and N-methyl-leucine, and $H_2O$ from molecular ion), m/z 732, m/z 578, m/z 552 (loss of valine, O-methylphenylserine, alanine, and N-methyl leucine from $H_2O$ from the molecular ion), m/z 475, m/z 144 (N-methyl-δ-hydroxyleucine), m/z 100 (valine), m/z 72 (alanine). The absolute stereochemistry of C-9, C-12 and C-18 were determined as L by acid hydrolysis of cyclomarin. The chirality of C-6 and C-15 were determined to be L due to the NOE signal enhancements of 60-H (2.6%, and 47-H (5.3%) by irradiation of 63-H and 46-H respectively.

Cyclomarin-A contains L-alanine, L-valine, L-N-methyl-L-leucine and 4 uncommon amino acids 12,O-methylphenyl L-serine, N-methyl-δ-hydroxy leucine, L-2-amino-3,5-dimethyl hex-4-enoic acid, and 1-(1,1-dimethyl-2,3-epoxypropyl) β-hydroxytryptophan. Particularly interesting is the presence of 1-(1,1-dimethyl-2,3-epoxypropyl) β-hydroxytryptophan, an uncommon amino acid biogenetically related to L-1-(1,1-dimethyl-2,3-epoxypropyl) tryptophan. The latter has been reported as constituent of the ilamycin antibiotics. (Y. Iitaka et al, *Acta Crystallogr.*, Sec B, 30, 2817 (1974)).

Cyclomarin-A is produced by a *Streptomyces sp.* bacterium which has been isolated from sediment found in marine estuaries located in southern California.

The *Streptomyces sp.* which produces cyclomarin-A is located in marine estuaries in coastal waters in and around San Diego, Calif. For example, the cyclo-marin-A producing *Streptomyces sp.* has been isolated from sediment located in estuaries in Mission Bay and Del Mar. The bacterial cultures isolated from these areas have been identified as CNB-982 and CNB-382, respectively. These cultures, along with other cultures of cyclomarin-A producing *Streptomyces sp.* isolated from marine estuaries around San Diego are maintained at the Scripps Institute of Oceanography at the University of California, San Diego, La Jolla, Calif. The cyclomarin-A producing *Streptomyces sp.* are naturally occurring bacteria which occur in abundant supplies in marine estuaries in the San Diego area including both Mission Bay and Del Mar. Samples of the CNB-982 bacterial culture were deposited with American Type Culture Collection (12301 Parklawn Drive, Rockville, Md. 20852 USA) on Feb. 14, 1995. The deposited CNB-982 cultures have been assigned ATCC deposit No. 55656.

The procedure used for isolating the cyclomarin-A producing *Streptomyces sp.* from the marine sediment can be any of the procedures commonly used to isolate bacteria from sediment. An exemplary procedure involves taking a 1 gram sample of sediment obtained from the top of the estuary floor and diluting this sample ten-fold with sterile seawater and plating these diluted materials onto a seawater based nutrient agar medium (supplemented with cyclohexamide and rifampacin to favor actinomycete growth). The inocula is spread with a sterile glass rod and actinomycetes colonies can be observed growing on the agar surface after 10 to 20 days of room temperature incubation.

The identifying characteristics of the cyclomarin-A producing *Streptomyces sp.* are best quantified by the fatty acid profiles shown in Table 2. The culture possesses yellow to cream vegetative mycelia and white spores. Further, positive identification of the *Streptomyces sp.* is provided by its ability to produce cyclomarin-A when fermented in seawater-based media.

in this specification, "biologically-purified" means that the bacterium or cyclomarin-A has been extracted or otherwise separated from its naturally occurring condition to form a purified composition which contains the uncontaminated bacterium or cyclomarin-A.

The extraction of cyclomarin-A from the fermentation broth may be conducted according to any of the conventional separation techniques.

Cyclomarin-A can be directly extracted from the fermentation broth by replicate ethylacetate liquid extraction. Cyclomarin-A is subsequently isolated from the crude ethylacetate extract by combined chromatographic methods. The extract is first fractionated with a vacuum activated silica gel column. Solvents typically utilized are isooctane ethylacetate mixtures. Fractions rich in cyclomarin-A are subjected to high performance liquid chromatography using five micron silica columns operating in semi-preparative mode. A peak representing pure cyclo-marin-A is subsequently obtained using 70 to 90 percent ethylacetate-isooctane mixtures. Final

TABLE 2

Fatty Acid Profile of Marine Bacterium CNB-382 (Streptomyces sp.)

| RT | Area | Ar/Ht | Respon | Ct | Name | % | Comment 1 | Comment 2 |
|---|---|---|---|---|---|---|---|---|
| 1.683 | 3644700 | 0.071 | — | 7.020 | SOLVENT PEAK | — | (min rt | |
| 1.949 | 713 | 0.031 | — | 7.555 | — | — | (min rt | |
| 2.017 | 583 | 0.026 | — | 7.692 | — | — | (min rt | |
| 6.458 | 692 | 0.034 | 1.035 | 12.612 | 13:0 ISO | 0.18 | ECL deviates 0.000 | Reference 0.003 |
| 6.739 | 16952 | 0.038 | 0.999 | 13.617 | 14:0 ISO | 4.76 | ECL deviates −0.001 | Reference 0.002 |
| 7.268 | 2144 | 0.039 | 0.987 | 13.999 | 14:0 | 0.63 | ECL deviates −0.001 | Reference 0.001 |
| 7.933 | 809 | 0.045 | 0.975 | 14.439 | 15:1 ISO G | 0.24 | ECL deviates −0.002 | |
| 8.066 | 1372 | 0.041 | 0.978 | 14.526 | 15:1 ANTEISO A | 0.40 | ECL deviates 0.000 | |
| 8.213 | 27076 | 0.041 | 0.971 | 14.622 | 15:0 ISO | 7.84 | ECL deviates 0.001 | Reference 0.0003 |
| 8.351 | 54724 | 0.042 | 0.968 | 14.712 | 15: ANTEISO | 15.82 | ECL deviates 0.001 | Reference 0.003 |
| 8.791 | 8026 | 0.042 | 0.962 | 14.999 | 15:0 | 2.30 | ECL deviates −0.001 | Reference 0.001 |
| 9.646 | 12681 | 0.056 | 0.952 | 15.454 | 16:1 ISO N | 3.60 | ECL deviates −0.007 | |
| 9.834 | 90770 | 0.043 | 0.949 | 15.628 | 16:0 ISO | 25.70 | ECL deviates 0.002 | Reference 0.003 |
| 10.144 | 16811 | 0.044 | 0.945 | 15.815 | 16:1 CIS 9 | 4.74 | ECL deviates −0.002 | |
| 10.450 | 44605 | 0.045 | 0.942 | 15.999 | 16:0 | 12.52 | ECL deviates −0.001 | Reference 0.000 |
| 11.169 | 8247 | 0.045 | 0.936 | 16.415 | 16:0 9? METHYL | 2.30 | ECL deviates −0.001 | |
| 11.358 | 8593 | 0.050 | 0.934 | 16.525 | 17:1 ANTEISO C | 2.40 | ECL deviates −0.000 | |
| 11.539 | 14347 | 0.046 | 0.933 | 16.630 | 17:0 ISO | 8.99 | ECL deviates −0.001 | Reference 0.001 |
| 11.698 | 32844 | 0.046 | 0.932 | 16.722 | 17:0 ANTEISO | 9.13 | ECL deviates −0.000 | Reference 0.000 |
| 11.818 | 3488 | 0.048 | 0.931 | 16.791 | 17:1 CIS 9 | 0.97 | ECL deviates −0.001 | |
| 11.981 | 1431 | 0.076 | 0.930 | 16.887 | 17:0 CYCLO | 0.40 | ECL deviates −0.001 | Reference 0.001 |
| 12.178 | 1695 | 0.046 | 0.928 | 17.000 | 17:0 | 1.38 | ECL deviates −0.000 | Reference 0.000 |
| 12.894 | 856 | 0.045 | 0.924 | 17.407 | 17:0 IOMETHYL | 0.24 | ECL deviates −0.003 | |
| 13.290 | 952 | 0.045 | 0.922 | 17.632 | 18:0 ISO | 0.26 | ECL deviates −0.000 | Reference −0.001 |
| 13.939 | 992 | 0.045 | 0.919 | 18.001 | 18:0 | 0.27 | ECL deviates 0.001 | Reference 0.000 |

| Solvent Ar | Total Area | Named Area | % Named | Total Amnt | Nbr Ref | ECL Deviation | Ref ECL Shift |
|---|---|---|---|---|---|---|---|
| 35447000 | 351907 | 351907 | 100.00 | 335058 | 14 | 0.002 | 0.002 |

Cyclomarin-A is produced by fermentation of the bacterium in seawater-based media at room temperature for 7 days. The fermentation media should contain from 70-80 volume percent filtered seawater, 20-30 volume percent deionized water, 0.5 to 1.5 volume percent soluble starch, 0.2 to 0.6 volume percent yeast extract and 0.1 to 0.3 volume percent peptone. An exemplary media will contain about 74 volume percent filtered seawater, 24.4 volume percent deionized water, 1 volume percent soluble starch, 0.4 volume percent yeast extract and 0.2 volume percent peptone.

The fermentation of the cyclomarin-A producing bacterium is accomplished according to conventional seawater media growth procedures. The bacteria is typically incubated at room temperature (approximately 26° C.) on a rotary shaker at approximately 200 rpm for about 1 week.

The biologically-purified compositions in accordance with the present invention are prepared by extracting the cyclomarin-A from the fermentation broth. As used purification of cyclomarin-A is achieved by appropriate crystallization from the same solvents.

After extraction and separation, cyclomarin-A can be positively identified not only by its structure, but also by the identifying characteristics and NMR spectra set forth in this specification and in the Figures.

Cyclomarin-A has been found to exhibit topical anti-inflammatory activity. Accordingly, cyclomarin-A may be used alone or in combination with a pharmaceutically acceptable carrier in the treatment of tissue inflammation. The carriers used in combination with cyclomarin-A can be any of the pharmaceutically acceptable carriers including saline, liposomes, organic based oils, ethanol, glycerol, propylene glycol and the like. Any of the conventional carrier compositions used in combination with anti-inflammatory agents may be suitable. The dosage levels may also be varied depending upon the extent of inflammation and other factors. Cyclomarin-A may be applied topically or given intravenously, intramuscularly, intrathecaly and direct injection into joints.

Cyclomarin-A may also be used in skin cremes. A small amount of cyclomarin-A, on the order of a few weight percent, is added to ointments, cremes, emulsions or other suitable skin moisturizing bases. Cyclomarin-A may be added to the skin creme in a semi-purified form. Cyclo-marin-A is preferably added to skin cremes which include moisturizers and other conventional skin creme ingredients.

In an exemplary fermentation, CNB-382 bacterium was cultured in eleven one-liter flasks at room temperature for 7–8 days. The fermentation broth was made up of 75% seawater, 25% DI water, 1% starch, 0.4% yeast extract and 2% peptone.

On the 8th day, the fermentation broths were harvested to give 8–12 mg/liter of cyclomarin-A. Cyclomarin-A was isolated from the broths by extraction with EtOAc (11 liters×2). The combined EtOAc extracts were concentrated to a light brown residue (650 mg), which was applied on a LH-20 column and eluted with MeOH to give 200 mg. Trituration with ether provided unsoluble white power (120 mg, fraction A) and ether soluble filtrate (fraction B, 80 mg). Fraction A and B were further purified with prep. TLC (silica gel, 1 mm thickness, EtOAc-MeOH 10:1) to yield cyclomarin-A (76 mg and 25 mg, respectively).

The fermentation broths were assayed by Hewlett Packard 1090 liquid chromatography. The optimized time for harvest was determined to be on the 8th day of fermentation. Optical rotations were recorded with a Perkin Elmer 141 polarimeter. Infrared and ultraviolet spectra were measured on a Perkin Elmer 1600 FTIR and Perkin Elmer Lambda 3B UV/VIS spectrophotometers, respectively. $^1$H and $^{13}$C NMR spectra were taken on either Brucker 200 or Varian 500 NMR spectrometers using solvent peaks as references. High resolution FAB mass spectra were determined by Midwest MS Center. EIMS were measured on a Hewlett Packard GC/MS 5890 spectrometer by direct sample inlet. HMQC and HMBC spectra were recorded using general pulse sequences described in the literature (M. F. Summers, L. G. Marzilli, A. Box, *J. Am. Chem. Soc.*, 108, 4285 (1986)).

Cyclomarin-A was obtained by the above fermentation/extraction as colorless fine crystals from acetone/ether. Assay results are as follows: $[\alpha]_D = -51.7°$ (CHCl$_3$, c=0.48), UV $\lambda$ max MeOH (log $\epsilon$) 222 (4.36), 287 (3.99), 293 (4.05); IR $\nu$ (neat) 3400–3300, 3030, 2962, 2928, 2871, 1644 (strong), 1512, 1453, 748 cm$^{-1}$, HR-FAB mass: obs, 1025.6062 (M-H$_2$O+1), calc. 1025.6057, required for C$_{56}$H$_{82}$O$_{11}$N$_8$; EI-MS m/z (rel. int.) 814 (0.1), 732 (1), 731 (1), 578 (0.1), 552 (0.1), 475 (0.4), 459 (2), 368 (3), 313 (4), 282 (16), 236 (4), 230 (5), 229 (35), 186 (21), 182 (1.2), 144 (69, N-methyl-δ-hydoxyleucine), 121 (100), 116 (33), 111 (7), 101 (11) 100 (96, valine), 85 (39) , 83 (39) , 72 (32, alanine). $^1$H-NMR δ (DMSO-d$_6$, 500 MHz): 4.35 (d, J=9 Hz, 1H, H-3) , 8.99 (brs, 1H, NH-4) , 4.63 (t, J=10 Hz, 1H, H-6) , 8.34 (d, J=10Hz, 1H, NH-7), 5.17 (brd, J=10 Hz, 1H, H-9), 4.42 (d, J=9 Hz, 1H, H-12), 9.20 (d, J=7 Hz, 1H, NH-13), 4.84 (dd, J=7.5, 2.5 Hz, 1H, H-15), 7.15 (d, J=8 Hz, 1H, NH-16), 4.12 (m, 1H, H-18), 8.29 (d, J=10.5, Hz, 1H, NH-19), 4.52 (d, J=13 Hz, 1H, H-21), 1.44 (m, 1H, H-22), 1.00 ( 1H, H-23 ), 2.34 (m, 1H, H-24 ), 2.53 (m, 1H, H-24 ), 0.21 (d, J=7 Hz, 3H, H-25), 5.13 (d, J=9 Hz, 1H, H-26), 7.78 (d, J=8 Hz, 1H, H-29) , 6.96 (t, J=8 Hz, 1H, H-30) , 7.07 (t, J=8 Hz, 1H, H-31), 7.72 (d, J=8 Hz, 1H, H-32), 7.10 (s, 1H, H-35) , 3.19 (dd, J=3, 4 Hz, 1H, H-37) , 2.85 (dd, J=4, 4.5 Hz, 1H, H-38), 2.87 (dd, J=4.5, 3 Hz, 1H, H-38), 1.40 (s, 3H, H-39), 1.57 (s, 3H, H-40), 2.68 (m, 1H, H-41), 5.00 (d, J=9.5 Hz, H-42), 1.71 (s, 3H, H-44), 1.58 (s, 3H, H-45), 0.88 (d, J=7 Hz, 3H, H-46), 2.26 (m, 1H, H-47), 1.55 (m, 1H, H-48, 0.96 (d, J=7 Hz, 3H, H-49), 0.94 (d, J=6.5, 3H, H-50), 2.30 (s, 3H, H-51), 2.24 (m, 1H, H-52), 1.04 (d, J=6.5 Hz, 3H H-53), 0.86 (d, J=7 Hz, 3H, H-54), 4.89 (d, J=2.5 Hz, 1H, H-55), 7.25–7.27 (5H, H-57, 58, 59, 60, 61), 3.05 (s, 3H, OMe), 0.76 (d, J=7.5 Hz), 3H, H-63), 2.72 (s, 3H, H-64), 4.04 (t, J=5.5 Hz, 1H, OH-24), 5.82 (brs, 1H, OH-26); $^{13}$C NMR δ (DMSO-d$_6$, 50 MHz): 57.1 (CH, C-3), 171.2 (C, C-5), 57.2 (CH, C-6, 167.6 (C, C-8,11), 58.2 (CH, C-9), 55.4 (CH, C-12), 170.0 (C, C-14), 55.8 (CH, C-15), 169.6 (C, C-17), 50.4 (CH, C-18), 169.4 (C, C-20), 57.0 (CH, C-21), 32.0 (CH, C-23), 66.5 (CH$_2$, C-24), 15.2 (CH3, C-25), 69.0 (CH, C-26), 113.2 (C, C-27), 127.4 (C, C-28), 121.5 (CH, C-29), 121.3 (CH, C-31), 113.1 (CH, C-32), 135.2 (C, C-33), 123.8 (CH, C-35), 57.6 (CH, C-37), 44.8 (CH$_2$, C-38), 22.4 (CH$_3$, C-39), 24.2 (CH$_3$, C-40), 35.8 (CH, C-41) , 125.7 (CH, C-42) , 132.2 (C, C-43) , 25.7 (CH$_3$, C-44) , 24.4 (CH$_3$, C-45), 18.5 (CH$_3$, C-46), 39.4 (CH$_2$, C-47), 29.8 (CH, C-48, 52), 22.6 (CH$_3$, C-49), 23.5 (CH3, C-50), 28.4 (CH$_3$, C-51), 29.8 (CH, C-52), 19.4 (CH$_3$, C-53), 19.8 (CH$_3$, C-54), 83.5 (CH, C-55), 137.2 (C, C-56), 126.7 (CH, C-57, 61), 127.8 (CH, C-58, 60), 127.6 (CH, C-59), 57.5 (CH$_3$, C-62), 20.2 (CH$_3$, C-63), 28.9 (CH$_3$, C-64).

Cyclomarin-A (5 mg) was hydrolyzed with 6N HCl (1 ml) under nitrogen at 110° C. for 24 hours in a sealed tube. The reaction mixture was concentrated under reduced pressure below 40° C. to evaporate HCl. The hydrolyzate was dissolved in MeOH and separated on a preparative TLC plate (silica gel, 0.25 mm thickness, CH$_2$Cl$_2$-MeOH-25% NH$_4$OH, 4:4:1). The amino acid bands were cut out and washed with H$_2$O-MeOH (1:1) to provide 3 fractions, which were identified as alanine, valine and N-methyl leucine by $^1$H NMR spectra and compared with authentic samples. Chiral TLC analysis (HPTLC-CHIR, Merck) using a solvent mixture of Me$_2$CO-MeOH-H$_2$O (5:1:1) against authentic D and L standards (Sigma) showed all three amino acids to have L configurations.

Cyclomarin-A was also acetylated as follows: Acetic anhydride (0.5 ml) was added to a solution of cyclomarin (25 mg) in pyridine (0.5 ml). The mixture was reacted at room temperature for 4 hours. The reaction mixture was poured into iced H$_2$O and extracted with EtOAc (20 ml×3). The combined EtOAc extract was reduced under vacuum to give a residue, which was purified on a preparative TLC plate (silica gel 1 mm thickness, developed with EtOAc) to furnish the diacetate (14 mg).

HR-FAB mass: obs. 1067.6173 (M-AcOH +1), calc. 1067.6162, required for C$_{60}$H$_{86}$O$_{13}$N$_8$; 1H-NMRδ (CDC13, 500 MHz): 4.79 (dd, J=9.5, 4.5 Hz, 1H, H-3), 6.75 (s, J=4 Hz, 1H, NH-4), 4.05 (t, J=10 Hz, 1H, H-6), 8.01 (d, J=10 Hz, 1H, NH-7), 4.45 (d, J=12.5, 3.5 Hz, 1H, H-9), 4.40 (dd, J=9.5, 8.5 Hz, 1H, H-12), 7.95 (d, J=7.5 Hz, 1H, NH-13), 4.88 (dd, J=5, 4.5 Hz, 1H, H-15), 7.08 (d, J=5 Hz, 1H, NH-16), 4.72 (dd, J=9.5, 6.5 Hz, 1H, H-18), 8.05 (d, J=9.5 Hz, 1H, NH-19), 4.95 (dd, J=10.5, 3.5 Hz, 1H, H-21), 2.36 (m, 1H, H-22), 2.97 (dd, J=10, 6.5 Hz, 1H, H-24), 3.18 (dd, J=10.5, 7 Hz, 1H, H-24), 0.16 (d, J=7 Hz, 3H, H-25), 6.45 (d, J=9.5 Hz, 1H, H-26), 7.75 (d, J=8 Hz, 1H, H-29), 7.08 (t, J=8 Hz, 1H, H-30), 7.18 (t, J=8 Hz, 1H, H-31), 7.71 (d, J=8 Hz, 1H, H-32), 7.11 (s, 1H, H-35), 3.15 (t, J=4 Hz, 1H, H-37), 2.87 (t, J=4 Hz, 1H, H-38), 2.72 (dd, J=4, 2.5Hz, 1H, H-38), 1.47 (s, 3H, H-39), 1.58 (s, 3H, H-40), 4.75 (d, J=10 Hz, H-42), 1.69 (s, 3H, H-44), 1.22 (s, 3H, H-45), 0.62 (d, J=7 Hz, 3H, H-46), 0.97 (d, J=6.5 Hz, 3H, H-49), 1.00 (d, J=6.5, 3H, H-50), 2.84 (s, 3H, H-51), 1.08 (d, J=6.5 Hz, 3H, H-53), 0.96 (d, J=6.5 Hz, 3H, H-54), 5.03 (d, J=5.5 Hz, 1H, H-55), 7.16-7.23 (5H, H-57, 58, 59, 60, 61), 3.34 (s, 3H, OMe), 1.20 (d, J=7 Hz, 3H, H-63), 2.55 (s, 3H, H-64),; $^{13}$C NMR δ (CDCl$_3$, 50 MHz): 168.7 (C, C-2), 54.65 (CH, C-3), 170.7 (C, C-5), 58.22 (CH, C-6), 168.17 (C, C-8), 58.22 (CH, C-9), 171.1 (C, C-11), 55.51 (CH, C-12), 169.66 (C, C-14), 55.9 (CH, C-15), 172.34 (C, C-17), 50.75 (CH, C-18), 168.64 (C, C-20), 58.95 (CH, C-21), 32.07 (CH$_2$, C-22), 28.38 (CH, C-23), 68.96 (CH$_2$, C-24), 15.23 (CH$_3$, C-25), 72.03 (CH, C-26), 107.79 (C, C-27), 127.15 (C, C-28), 120.46 (CH, C-29, 30), 122.38 (CH, C-31), 113.84 (CH, C-32), 135.84 (C, C-33), 57.63 (C, C-36), 57.45 (CH, C-37), 45.37 (CH$_2$, C-38), 23.12 (CH$_3$, C-39), 24.47 (CH$_3$, C-40), 35.25 (CH, C-41), 124.74 (CH, C-42), 134.41 (C, C-43), 25.76 (CH$_3$, C-44), 18.93 (CH$_3$, C-45), 18.45 (CH$_3$, C-46), 38.92 (CH$_2$, C-47), 25.76 (CH, C-48), 22.61 (CH$_3$, C-49), 23.48 (CH$_3$, C-50), 29.55 (CH$_3$, C-51), 30.84 (CH, C-52), 19.41 (CH$_3$, C-53), 19.97 (CH$_3$, C-54), 80.05 (CH, C-55), 135.09 (C, C-56), 127.86 (CH, C-57, 61), 128.33 (CH, C-58, 60), 128.75 (CH, C-59), 57.76 (CH$_3$, C-62), 20.65 (CH$_3$, C-63), 29.13 (CH$_3$, C-64), HMBC data: (H25-C22, 23, 24), (H29-C33), (H30-C28, 32), (H32-C28, 30), (H35-C27, 28, 33), (H39-C36, 37, 40), (H40-C36, 37, 39), (H44-C42, 43), (H45-C42, 43), (H46-C42), (H49-C47, 48), (H51-C11), (H53-C52, 54), (H54-C52), (H63-C17, 18), (H64-C2), (1.90-OAc24), (2.10-OAc26), (OMe-C55).

Examples of practice demonstrating the anti-inflammatory effectiveness of cyclomarin-A are as follows.

Cyclomarin-A was tested by measuring inhibition of phorbol-induced inflammation (edema) of mouse ears. This is a conventional test which has been accepted as demonstrating a compound's effectiveness in reducing inflammation. The compound is topically applied in acetone to the inside pinnae of the ears of mice in a solution containing the edema-causing irritant, i.e. phorbol 12-myristate 13-acetate (PMA). PMA alone (2 microgram per ear) or in combination with varying amounts of cyclomarin-A was applied to the left ears of (5 mice per treatment group). Acetone was applied to all right ears. After a 3-hour and 20-minute incubation at 23° C., the mice were sacrificed, the ears removed and bores taken and weighed. Edema was measured by subtracting the weight of the right ear (acetone control) from the weight of the left ear (treated). The results were recorded as a percent decrease (inhibition) or percent increase (potentiation) in edema relative to the PMA control group edema. The results are summarized in Tables 3-5.

TABLE 3

| Inhibition of Mouse Ear Edema - Standard Protocol | |
|---|---|
| Dose (ug/ear) | Inhibition |
| 100 | 96.2 |
| 50 | 88.0 |
| 25 | 57.0 |
| 10 | 39.0 |
| 5 | 3.0 |

TABLE 4

| Inhibition of Mouse Ear Edema - Time of Addition Study | | |
|---|---|---|
| Dose (ug/ear) | Time (mins) | Inhibition |
| 50 | −60 | 51.8 |
| 50 | −30 | 79.4 |
| 50 | 0 | 82.8 |
| 50 | +30 | 50.9 |
| 50 | +60 | 12.0 |

TABLE 5

| Inhibition of Mouse Ear Edema - Systemic Study | | |
|---|---|---|
| Dose (mg/kg) | Administration | Inhibition |
| 100 | IP, 1 hour prior | 48.0 |
| 50 | IP, 1 hour prior | 55.0 |
| 25 | IP, 1 hour prior | 28.0 |

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the above preferred embodiments, but is only limited by the following claims.

What is claimed is:

1. A biologically purified composition of matter comprising a cyclic depsipeptide identified as cyclo-marin-A which has the structure

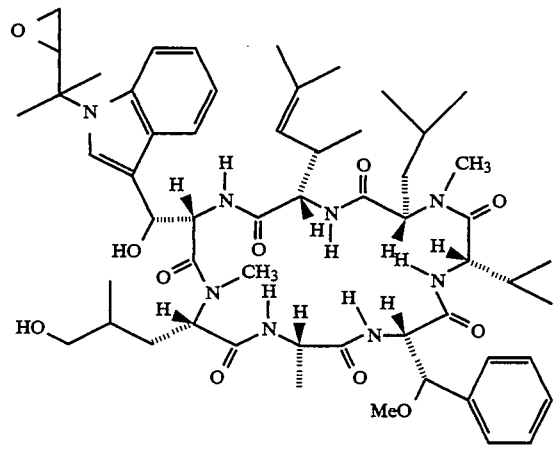

2. A biologically purified composition according to claim 1 consisting essentially of cyclomarin-A and a pharmaceutically acceptable carrier.

3. A composition for use as an anti-inflammatory agent in treating mammals, said composition consisting essentially of an effective amount of a cyclic heptapeptide according to claim 1 and a pharmaceutically acceptable carrier for said cyclic heptapeptide.

4. A method for treating mammals having inflamed tissue to reduce inflammation which comprises:
    administering to said mammal an inflammation reducing effective amount of a composition comprising a cyclic heptapeptide according to claim 1.

5. A method for treating mammals having inflamed tissue to reduce inflammation which comprises:
    administering to said mammal an inflammation reducing effective amount of a composition according to claim 3.

* * * * *